(12) United States Patent
Shibatani et al.

(10) Patent No.: US 6,514,962 B1
(45) Date of Patent: Feb. 4, 2003

(54) STABILIZED PREPARATIONS OF β-LACTAM ANTIBIOTIC

(75) Inventors: Hatsuo Shibatani, Ushiku (JP); Tomoyasu Nakamura, Chiba (JP)

(73) Assignee: Takeda Schering-Plough Animal Health K.K., Osaka (JP)

( * ) Notice: Subject to any disclaimer, the term of this patent is extended or adjusted under 35 U.S.C. 154(b) by 0 days.

(21) Appl. No.: 09/774,186

(22) PCT Filed: Jun. 16, 1999

(86) PCT No.: PCT/JP99/03233

§ 371 (c)(1),
(2), (4) Date: Feb. 5, 2001

(87) PCT Pub. No.: WO00/07628

PCT Pub. Date: Feb. 17, 2000

(30) Foreign Application Priority Data

Aug. 4, 1998 (JP) .............................. 10-220161

(51) Int. Cl.[7] .................. A61K 42/24; A61K 47/44; A61K 31/43; A61K 9/14; A61K 31/545

(52) U.S. Cl. ................... 514/210.02; 514/210.03; 514/210.04; 514/210.05; 514/210.06; 514/210.07; 514/210.08; 514/210.09; 514/210.1; 514/210.11; 514/210.12

(58) Field of Search .................. 514/0.02, 0.03, 514/0.04, 0.05, 0.06, 0.07, 0.08, 0.09, 0.1, 1.11, 0.12, 0.13, 0.14, 0.15

(56) References Cited

U.S. PATENT DOCUMENTS

| 4,731,362 A | | 3/1988 | Hamashima et al. | |
|---|---|---|---|---|
| 5,063,074 A | * | 11/1991 | Kahn et al. | 426/585 |
| 5,595,762 A | | 1/1997 | Derrieu et al. | |
| 5,744,465 A | * | 4/1998 | Lin et al. | 514/210 |

FOREIGN PATENT DOCUMENTS

| EP | 0 564 270 | 10/1993 |
|---|---|---|
| JP | 61-115031 | 6/1986 |
| JP | 62-89619 | 4/1987 |
| JP | 6-298769 | 10/1994 |

OTHER PUBLICATIONS

Patent Abstracts of Japan, JP 59–176209, Oct. 5, 1984.

* cited by examiner

*Primary Examiner*—Richard L. Raymond
*Assistant Examiner*—Thomas C McKenzie
(74) *Attorney, Agent, or Firm*—Oblon, Spivak, McClelland, Maier & Neustadt, P.C.

(57) ABSTRACT

Stabilized preparations which contain a β-lactam antibiotic having an esterified carboxyl group attached directly to the mother nucleus, an oil and a phosphate.

15 Claims, No Drawings

STABILIZED PREPARATIONS OF β-LACTAM ANTIBIOTIC

TECHNICAL FIELD

This invention relates to a stabilized preparation of a β-lactam antibiotic having an esterified carboxy group directly coupled to the nucleus.

BACKGROUND ART

Since β-lactam antibiotics, particularly penicillin antibiotics, are generally allergenic, it is common practice to have them granulated, for instance, to prevent scattering but the practice is not effective enough in preventing scattering. Therefore, the inventors of this invention explored the feasibility of formulating them into oil-containing preparations. However, there is the problem that β-lactam antibiotics having an esterified carboxy group directly coupled to the nucleus are generally thermo-labile in oil-containing compositions.

This invention has been made to solve the above problem, with its object being to provide a stabilized preparation of a β-lactam antibiotic having an esterified carboxy group directly coupled to the nucleus which is stable against heat even in an oil-including formulation.

DISCLOSURE OF INVENTION

The inventors of this invention did much research to overcome the above stability problem of β-lactam antibiotics having an esterified carboxy group directly coupled to the nucleus and found for the first time that when a β-lactam antibiotic having an esterified carboxy group directly coupled to the nucleus is mixed with a salt of phosphoric acid and oil, a dramatic improvement occurs in its stability.

This invention is carried into practice by mixing a β-lactam antibiotic having an esterified carboxy group directly coupled to the nucleus with a salt of phosphoric acid and oil. While this mixing is carried out using a kneading-machine or the like, the resulting mixture is generally in the form of a paste. This paste can be put to use as it is but is preferably processed into various dosage forms in the routine manner.

The β-lactam antibiotic having an esterified carboxy group directly coupled to the nucleus includes those antibiotics having an ester moiety comprising a group of the formula:

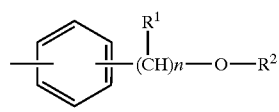

(wherein $R^1$ means hydrogen or a lower ($C_1$—$C_6$) alkyl group such as methyl, ethyl or the like, n means an integer of 0–3, $R^2$ means a $C_1$—$C_{10}$ alkanoyl group (e.g. a lower ($C_1$—$C_6$) alkanoyl group such as acetyl, propionyl, butyryl, isobutyryl or the like)); a carboxymethyl group of the formula:

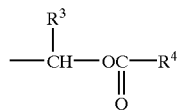

(wherein $R^3$ means hydrogen or a lower alkyl group such as methyl, ethyl or the like, $R^4$ means a straight-chain or branched lower ($C_1$—$C_6$) alkyl group such as methyl, ethyl or the like); or a group of the formula:

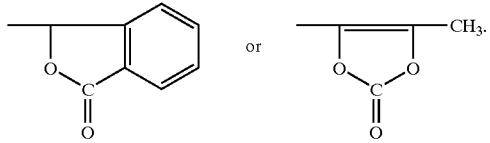

The β-lactam antibiotic having an esterified carboxy group directly coupled to the nucleus includes carboxylic acid esters of penicillin and carboxylic acid esters of cephalosporin; for example, such antibiotics in the penicillin series as tobicillin, talampicillin, pivampicillin, becampicilin, pivmecillinam, bacmecillinam, lenampicillin, sultamicillin, etc. and such antibiotics in the cephalosporin series as cefotiam hexetil, cefetamet pivoxil, cefpodoxime proxetil, cefteram pivoxil and cefuroxime axetil, among others.

The oil may for example be a naturally-occurring fish oil or vegetable oil. As an alternative, it may be a synthetic oil such as silicone oil. More particularly, the vegetable oil includes soybean oil, linseed oil, sesame oil, corn oil, rapeseed oil, olive oil, caster oil, peanut oil, coconut oil, etc., and the fish oil includes sardine oil, salmon oil, mackerel oil, saury oil, liver oil (granulose shark, codfish, skipjack, Pacific flying squid, yellowtail), etc. Aside from the above, sperm oil (seiwhale, humpjack whale, fin whale, blackfish) may also be used. Among these, soybean oil of the composition defined in Japanese Pharmacopoeia is preferred.

On the other hand, as the salt of phosphoric acid, there can be mentioned alkaline earth metal salts of phosphoric acid, such as aluminum phosphate, barium phosphate (primary, secondary and tertiary), calcium phosphate (primary, secondary and tertiary), etc. and alkali metal salts of phosphoric acid, such as sodium phosphate (primary, secondary and tertiary). Among these, calcium phosphate and, in particular, tertiary calcium phosphate are conducive to particularly satisfactory results.

The stabilized preparation of the invention may be provided in the pasty form as mentioned above but is preferably used in the conventional pharmaceutical dosage forms such as powders, fine granules, granules, tablets, sugar-coated tablets, capsules, solutions and emulsions. Where necessary, the preparation may contain a diluent (excipient), a disintegrator (e.g. sucrose, lactose, starch, glucose, wheat bran, dextrin, crystalline cellulose, low-substitution-degree hydroxypropylcellulose, synthetic aluminum silicate, etc.), a binder (thickener) (e.g. cellulose, methylcellulose, hydroxypropylcellulose, hydroxypropylmethylcellulose, polypropylpyrrolidone, polyvinylpyrrolidone, gelatin, gum arabic, sodium alginate, polyethylene glycol, etc.), a coloring agent, a sweetener, a lubricant (e.g. magnesium stearate) and other additives.

It is also recommendable that the stabilized preparation of the invention be provided in the form of a powder prepared by mixing a β-lactam antibiotic having an esterified carboxy group directly coupled to the nucleus with said salt of phosphoric acid, then mixing the resulting mixture with oil and a surfactant (the resulting preparation is a paste), and adding a diluent (excipient) such as lactose.

The surfactant mentioned just above includes polyglycerol fatty acid esters, sucrose fatty acid esters, polyoxyethylene sorbitan fatty acid esters, polyethylene glycol fatty acid esters, polyoxyethylene alkyl ethers, polyoxyethylene hydrogenated castor oil, sorbitan fatty acid esters and polyoxyethylene-polyoxypropylene alkyl ethers, among others.

The recommended proportions of said β-lactam antibiotic having an esterified carboxy group directly coupled to the nucleus, said oil and said salt of phosphoric acid in the stabilized preparation of the invention are 5~50% (weight %; the same applied hereinafter) of the β-lactam antibiotic having an esterified carboxy group directly coupled to the nucleus, 1.5~60% of the oil, and not less than 1.5% of the salt of phosphoric acid.

The effect of the invention is now explained by way of the following test example.

TEST EXAMPLE

The following preparations were stored at 50° C., and compared for stability. (Each figure in the table represents the % residue of tobicillin relative to the initial baseline).

|  | 0.5 Month | 1 Month | 1.5 Months |
|---|---|---|---|
| Control preparation*1 | 101.2 | 68.1 | 33.2 |
| Example 4 | 99.1 | 92.7 | 88.7 |

*1The formulation of Example 4 minus tertiary calcium phosphate

|  | 0.5 Month | 1 Month | 1.5 Months |
|---|---|---|---|
| Control preparation*2 | 94.6 | 77.5 | 21.7 |
| Example 5 | 99.7 | 93.0 | 76.9 |

*2The formulation of Example 5 minus tertiary calcium phosphate

| Surfactant | 1 Month |
|---|---|
| Surfactant-free preparation*3 | 93.0 |
| Polyoxyethylene nonylphenyl ether*4 | 99.2 |
| Preparation of Example 6 | 99.1 |
| Polysorbate 20*5 | 93.5 |
| Polysorbate 80*6 | 93.9 |

*3The formulation of Example 6 minus surfactant
*4The same as the formulation of Example 6 except that Nonipol 100 (polyoxyethylene nonylphenyl ether manufactured by Sanyo Chemical Industries; the same applies hereinafter) was substituted for the surfactant polyoxyethylene hydrogenated castor oil.
*5, *6The same as the formulation of Example 6 except that Tween 20 or Tween 80 (Polysorbate 20 or Polysorbate 80 manufactured by Kao Corporation) was substituted for the surfactant polyoxyethylene hydrogenated castor oil.

It is apparent from the above results that the phosphate-supplemented oil-containing preparation of the invention is superior to the phosphate-free oil-containing preparation in thermal stability.

The stabilized preparation according to the present invention can be used to advantage as, for example, a drug for fish disease by adding it directly to raw fish meals or dissolving it in water and mixing the solution with fish feed such as dry pellets.

Some working examples of the invention are given below.
Example 1
To a mixture of 34.4 g of tobicillin and 3.4 g of tertiary calcium phosphate is added 10 g of soybean oil (Daizu Yu, Toho Pharmaceutical Ind.; the same applies below), and the whole mixture is kneaded to give a paste.
Example 2
To a mixture of 34.4 g of tobicillin and 3.4 g of tertiary calcium phosphate is added 10 g of cod liver oil (Hinomaru Marine Oil Sukesou (Alaska Pollack), manufactured by Nippon Suisan; the same applies below), and the whole mixture is kneaded to give a paste.
Example 3
To a mixture of 34.4 g of tobicillin and 3.4 g of tertiary calcium phosphate are added 5.2 g of soybean oil and 5 g of the surfactant NIKKOL HCO-60 (polyoxyethylene hydrogenated castor oil, manufactured by Nikko Chemicals Co., Ltd.; the same applies hereinafter), and the whole mixture is kneaded to give a paste.
Example 4
To a mixture of 34.4 g of tobicillin and 1.7 g of tertiary calcium phosphate are added 4.3 g of cod liver oil and 4.3 g of the surfactant Nonipol 100. The whole mixture is kneaded and, then, 55.3 g of lactose is added to give a powder.
Example 5
To a mixture of 34.4 g of tobicillin and 1.7 g of tertiary calcium phosphate are added 4.3 g of soybean oil and 4.3 g of the surfactant Nonipol 100. The mixture is kneaded and, then, 55.3 g of lactose is added to give a powder.
Example 6
To a mixture of 34.4 g of tobicillin and 3.4 g of tertiary calcium phosphate are added 5.2 g of soybean oil and 3.4 g of the surfactant NIKKOL HCO-60. The mixture is kneaded and, then, 53.6 g of lactose is added to give a powder.

What is claimed is:

1. A stabilized preparation comprising a β-lactam antibiotic having an esterified carboxy group directly coupled to the nucleus, oil and a salt of phosphoric acid.

2. The stabilized preparation according to claim 1, wherein the β-lactam antibiotic is a penicillin.

3. The stabilized preparation according to claim 2, wherein the penicillin is tobicillin.

4. The stabilized preparation according to claim 1 wherein the oil is soybean oil.

5. The stabilized preparation according to claim 1 wherein the salt of phosphoric acid is an alkaline earth metal salt of phosphoric acid.

6. A stabilized preparation comprising tobicillin, soybean oil and tertiary calcium phosphate.

7. A stabilized powder preparation comprising tobicillin, soybean oil, tertiary calcium phosphate, polyoxyethylene hydrogenated castor oil and lactose.

8. The stabilized preparation according to claim 2, wherein the penicillin is selected from the group consisting of tobicillin, talampicillin, pivampicillin, bacampicilin, pivmecillinam, bacemecillinam, lenampicillin, and sultamicillin.

9. The stabilized preparation according to claim 1, wherein β-lactam antibiotic is a cephalosporin.

10. The stabilized preparation according to claim 9, wherein the cephalosporin is selected from the group consisting of cefotiam hexetil, cefetamet pivoxil, cefpodoxime proxetil, cefteram pivoxil, and cefuroxime axetil.

11. The stabilized preparation according to claim 1, further comprising one or more additives selected from the group consisting of a diluent, a disintegrator, a binder, a coloring agent, a sweetener, a lubricant, and a surfactant.

12. The stabilized preparation according to claim 1, wherein the concentration of the β-lactam antibiotic ranges from 5 to 50 wt %.

13. The stabilized preparation according to claim 1, wherein the concentration of the oil ranges from 1.5 to 60 wt %.

14. The stabilized preparation according to claim 1, wherein the concentration of the salt of phosphoric acid is 1.5 wt % or more.

15. A method of making a stabilized preparation, comprising:
 a) mixing a β-lactam antibiotic having an esterified carboxy group directly coupled to the nucleus with a salt of phosphoric acid;
 b) mixing the mixture from step (a) with an oil and a surfactant;
 c) adding a diluent to mixture from step (b).

\* \* \* \* \*